US012788235B2

(12) United States Patent
Fettinger et al.

(10) Patent No.: US 12,788,235 B2
(45) Date of Patent: Nov. 10, 2026

(54) METHODS AND DEVICES FOR GAMMA CORRECTION

(71) Applicant: Boston Scientific Scimed, Inc., Maple Grove, MN (US)

(72) Inventors: Nathan S. Fettinger, Minneapolis, MN (US); Matthew Protas, Minneapolis, MN (US); Phillip C. Dingman, Shoreview, MN (US); Thomas M. Zappia, Jr., West Boylston, MA (US); Longquan Chen, Andover, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 15 days.

(21) Appl. No.: 18/774,052

(22) Filed: Jul. 16, 2024

(65) Prior Publication Data

US 2024/0366077 A1 Nov. 7, 2024

Related U.S. Application Data

(63) Continuation of application No. 17/393,007, filed on Aug. 3, 2021, now Pat. No. 12,064,089.

(Continued)

(51) Int. Cl.

*A61B 1/05* (2006.01)

*A61B 1/00* (2006.01)

(Continued)

(52) U.S. Cl.

CPC ........... *A61B 1/05* (2013.01); *A61B 1/00045* (2013.01); *G06T 5/92* (2024.01); *G06T 7/90* (2017.01);

(Continued)

(58) Field of Classification Search

CPC ..... A61B 1/05; A61B 1/00045; A61B 1/0676; G06T 5/92; G06T 7/90; G06T 2207/10024; G06T 2207/10068

See application file for complete search history.

(56) References Cited

U.S. PATENT DOCUMENTS

2008/0080784 A1 4/2008 Ozdemir

2009/0109284 A1 4/2009 Takayama et al.

(Continued)

FOREIGN PATENT DOCUMENTS

CN 109255760 A 1/2019

KR 1020040017654 A 2/2004

OTHER PUBLICATIONS

Imtiaz et al., "Image Enhancement and Space-Variant Color Reproduction Method for Endoscopic Images using Adaptive Sigmoid Function", 2014 36th Annual International Conference of the IEEE Engineering in Medicine and Biology Society, pp. 3905-3908, 4 pages, Aug. 2014.

(Continued)

*Primary Examiner* — Casey L Kretzer

(74) *Attorney, Agent, or Firm* — Seager, Tufte & Wickhem, LLP

(57) ABSTRACT

A medical system includes a shaft having a proximal end and a distal end, an imaging device at the distal end of the shaft, and a controller, the controller receives image data comprising pixel data from the imaging device, the pixel data including a plurality of individual pixel values, converts the pixel data from a RGB format to a $YC_bC_r$ format, and forms adjusted pixel data by applying a gain to the pixel data, wherein the gain is based on a Y value, a $C_b$ value, and a $C_r$ value of the individual pixel values of the converted pixel data.

17 Claims, 5 Drawing Sheets

Related U.S. Application Data

(60) Provisional application No. 63/060,885, filed on Aug. 4, 2020.

(51) Int. Cl.
*A61B 1/06* (2006.01)
*G06T 5/92* (2024.01)
*G06T 7/90* (2017.01)

(52) U.S. Cl.
CPC ... *A61B 1/0676* (2013.01); *G06T 2207/10024* (2013.01); *G06T 2207/10068* (2013.01)

(56) References Cited

U.S. PATENT DOCUMENTS

| | | | |
|---|---|---|---|
| 2010/0316289 | A1 | 12/2010 | Tsai |
| 2012/0209287 | A1 | 8/2012 | Zhao et al. |
| 2014/0107416 | A1 | 4/2014 | Birnkrant |
| 2015/0181185 | A1* | 6/2015 | Ikemoto ................ G06T 7/0012 348/71 |
| 2017/0155804 | A1 | 6/2017 | Kikuchi |
| 2018/0013999 | A1 | 1/2018 | Koshika et al. |
| 2018/0042469 | A1 | 2/2018 | Dresher et al. |

OTHER PUBLICATIONS

International Search Report and Written Opinion issued in PCT/US2021/044349 on Nov. 4, 2021, 12 pages.

* cited by examiner

METHODS AND DEVICES FOR GAMMA CORRECTION

CROSS-REFERENCE TO RELATED APPLICATIONS

This application is a continuation of U.S. Non-Provisional application Ser. No. 17/393,007, filed Aug. 3, 2021, which claims the benefit of priority from U.S. Provisional Application No. 63/060,885, filed on Aug. 4, 2020, which is incorporated by reference herein in its entirety.

TECHNICAL FIELD

The present disclosure relates generally to medical devices and methods of use. More particularly, in some embodiments, the disclosure relates to endoscopic imaging tools and methods related to enhancing images generated by an imaging device associated with the endoscope.

BACKGROUND

Medical tools, such as scopes or catheters, may include an associated imaging device, for example cameras or cameras associated with the medical scopes, for imaging body tissue. Drawbacks of scopes using such imaging devices include, for example, intensity gradients created when target objects vary in distance with the body and/or shadows created by objects blocking light to other structures within the body. There exist light controls for adjusting the light output globally from a light source, e.g., a light emitting diode (LED), to the target area. However, changing the amount of light from the light source may increase hotspots if the light output is increased, or increase shadows if the light output is decreased. Thus, there is a need to adjust for localized regions of an image to improve the overall visibility of the entire image. The disclosure may solve one or more of these problems or other problems in the art. The scope of the disclosure, however, is defined by the attached claims and not the ability to solve a specific problem.

SUMMARY OF THE DISCLOSURE

According to an aspect, a medical system includes a shaft having a proximal end and a distal end, an imaging device at the distal end of the shaft, and a controller, wherein the controller is configured to receive image data comprising pixel data from the imaging device, the pixel data including a plurality of individual pixel values, convert the pixel data from a RGB format to a $YC_bC_r$ format, and form adjusted pixel data by applying a gain to the pixel data, wherein the gain is based on a Y value, a $C_b$ value, and a $C_r$ value of the individual pixel values of the converted pixel data.

The controller may be further configured to calculate a magnitude (e.g., an intensity) for each pixel value, wherein the magnitude for each pixel value may be equal to $\sqrt{(Y^2+C_b^2+C_r^2)}$, and wherein the gain for an individual pixel component is a function of the magnitudes of all components.

The gain may include a first gain and a second gain, and the first gain may be applied to the Y value, and the second gain may be applied to both the $C_b$ value and the $C_r$ value of a corresponding pixel value.

The medical system may further include a memory, wherein the memory may include a look up table (LUT) for each of a luminance value and a chroma value.

The controller may be further configured to convert the adjusted pixel data from the $YC_bC_r$ format to the RGB format.

The medical system may further include a display, and wherein the controller may be further configured to generate an image based on the adjusted and converted pixel data.

The medical system may further include a light emitting device at the distal end of the shaft.

The medical system may further include a user input device configured to receive at least one user input for controlling the medical system.

The controller may include a field programmable gate array (FPGA).

The medical system may further include a handle, wherein the controller may be disposed on or in the handle.

According to an aspect, a method of controlling an imaging device for a medical system includes receiving an image comprising pixel data from an imaging device of the medical system, the pixel data including a plurality of individual pixel values, converting the pixel data from a RGB format to a second multi-channel color format, the second multi-channel color format having a brightness value and a color value, and calculating a magnitude for each pixel value, wherein the gain magnitude is based on the brightness value and the color value of each respective pixel, applying the gain magnitude to adjust the corresponding brightness or the corresponding color for each pixel, and converting each of the plurality of pixels from the second multi-channel color format to the RGB format.

The method may further include applying a different gain to the brightness value than the color value of a corresponding pixel value.

The method may further include generating an image on a display of the medical system based on the adjusted and converted pixel data.

The method may further include applying the gain to each pixel value includes matching the magnitude with a corresponding value in a brightness look up table (LUT) for a corresponding brightness value, and matching the gain magnitude with a corresponding value in a color LUT for a corresponding color value.

The gain magnitude may be applied to each of the brightness and the color values for the corresponding pixel.

According to an aspect, a non-transitory computer-readable medium storing instructions that, when executed by a computer, cause the computer to perform a method for processing electronic images from a medical system, the method including receiving an image comprising pixel data from an imaging device of the medical system, the pixel data including a plurality of individual pixel values, converting the pixel data from a RGB format to a $YC_bC_r$ format, and calculating a magnitude for each pixel value, wherein the gain magnitude for each pixel is equal to $\sqrt{(Y^2+C_b^2+C_r^2)}$, and wherein the gain magnitude is based on the Y value, the $C_b$ value, and the $C_r$ value of each respective pixel, applying the gain magnitude to adjust the corresponding luminance or the corresponding chroma for each pixel, and converting each of the plurality of pixels from the $YC_bC_r$ format to the RGB format.

The method may further include applying a different gain to the Y value than the $C_b$ value and the $C_r$ value of a corresponding pixel value.

The method may further include generating an image on a display of the medical system based on the adjusted and converted pixel data.

Applying the gain to each pixel value may include matching the magnitude with a corresponding value in a luminance look up table (LUT) for a corresponding Y value, and matching the gain magnitude with a corresponding value in a chroma LUT for a corresponding $C_b$ value and a corresponding $C_r$ value.

The gain magnitude may be applied to each of the luminance and the chroma values for the corresponding pixel.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
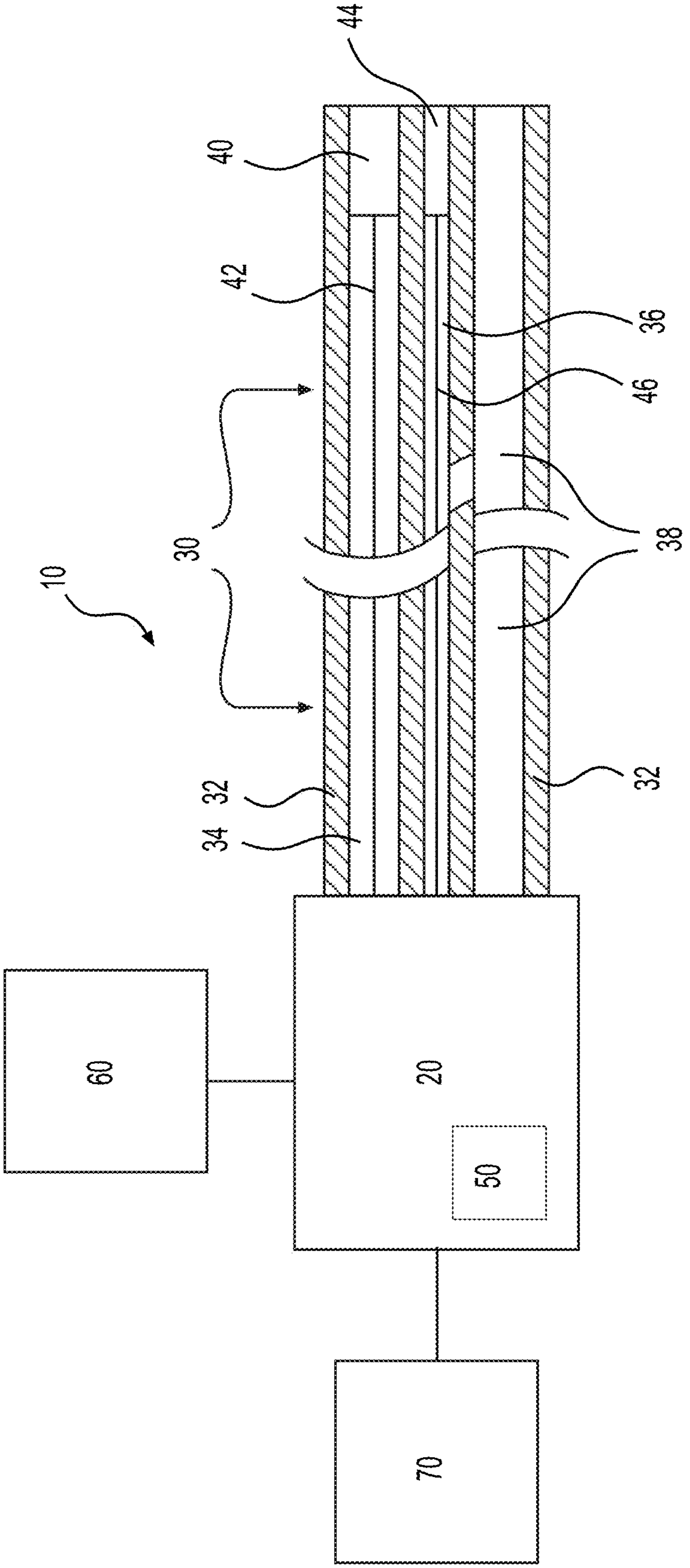
FIG. 1 is a schematic view of a medical system, according to an embodiment.

The disclosure is described with reference to an exemplary medical system and imaging device for imaging a target site and improving an overall brightness of one or more images created by the imager of the target site. However, it should be noted that reference to any particular procedure is provided only for convenience and not intended to limit the disclosure. A person of ordinary skill in the art would recognize that the concepts underlying the disclosed device and application method may be utilized in any suitable procedure, medical or otherwise. The disclosure may be understood with reference to the following description and the appended drawings, wherein like elements are referred to with the same reference numerals.

For ease of description, portions of the device and/or its components are referred to as proximal and distal portions. It should be noted that the term "proximal" is intended to refer to portions closer to a user of the device, and the term "distal" is used herein to refer to portions further away from the user. Similarly, extends "distally" indicates that a component extends in a distal direction, and extends "proximally" indicates that a component extends in a proximal direction. Further, as used herein, the terms "about," "approximately" and "substantially" indicate a range of values within +/−10% of a stated or implied value. Additionally, terms that indicate the geometric shape of a component/surface refer only to approximate shapes.

FIG. 1 schematically illustrates a medical system 10 that includes a handle 20, an access sheath 30 (shown in cross-section), a controller 50 located in or on handle 20 (the location is not limited thereto), a display 60, and a user input device, e.g., a graphical user interface (GUI), 70. Medical system 10 may be an endoscope system for imaging of and/or providing access to a target site in a body. For example, medical system 10 may be the SpyGlass™ DM System by Boston Scientific Corp., a ureteroscope, a renal sheath, a hysteroscope sheath, a cystoscopy sheath, a steerable sheath, or other scope.

Access sheath 30 may be, for example, a ureteral access sheath (e.g., Navigator™ Ureteral Access Sheath by Boston Scientific Corp.), a renal sheath, a hysteroscope sheath, a cystoscopy sheath, a steerable sheath, or other appropriate access sheath. Access sheath 30 may be formed of an extrusion having an outer sheath 32, and may have various diameters and lengths depending on the medical procedure and the body cavity being accessed during the medical procedure. Access sheath 30 may be inserted into a body opening, e.g., a natural orifice or an incision, and advanced to a target site to perform a medical procedure.

Access sheath 30 may include an imaging lumen 34 and a light lumen 36. A sensor or an imaging device 40 (e.g., a camera) may be fixed at a distal end of imaging lumen 34. An imaging cable 42 may extend proximally from imaging device 40 and may connect imaging device 40 to display 60, controller 50, and/or any other associated device. A light emitting device 44 (e.g., a LED) may be fixed at a distal end of light lumen 36. A light cable 46 may extend proximally from light emitting device 44 to controller 50, user input 70, and/or any other associated devices. As shown in FIG. 1, access sheath 30 may include a working channel 38 through which medical instruments or other tools may be inserted. It will be understood that imaging device 40 and/or light emitting device 44 are not required to be fixed at the distal end of access sheath 30, and each of imaging device 40 and/or light emitting device 44 may be movable within respective lumens 34 and 36. Alternatively, light emitting device 44 and imaging device 40 may be formed as a single unit and may be disposed within and/or at a distal end of a single lumen.

Figure 2:
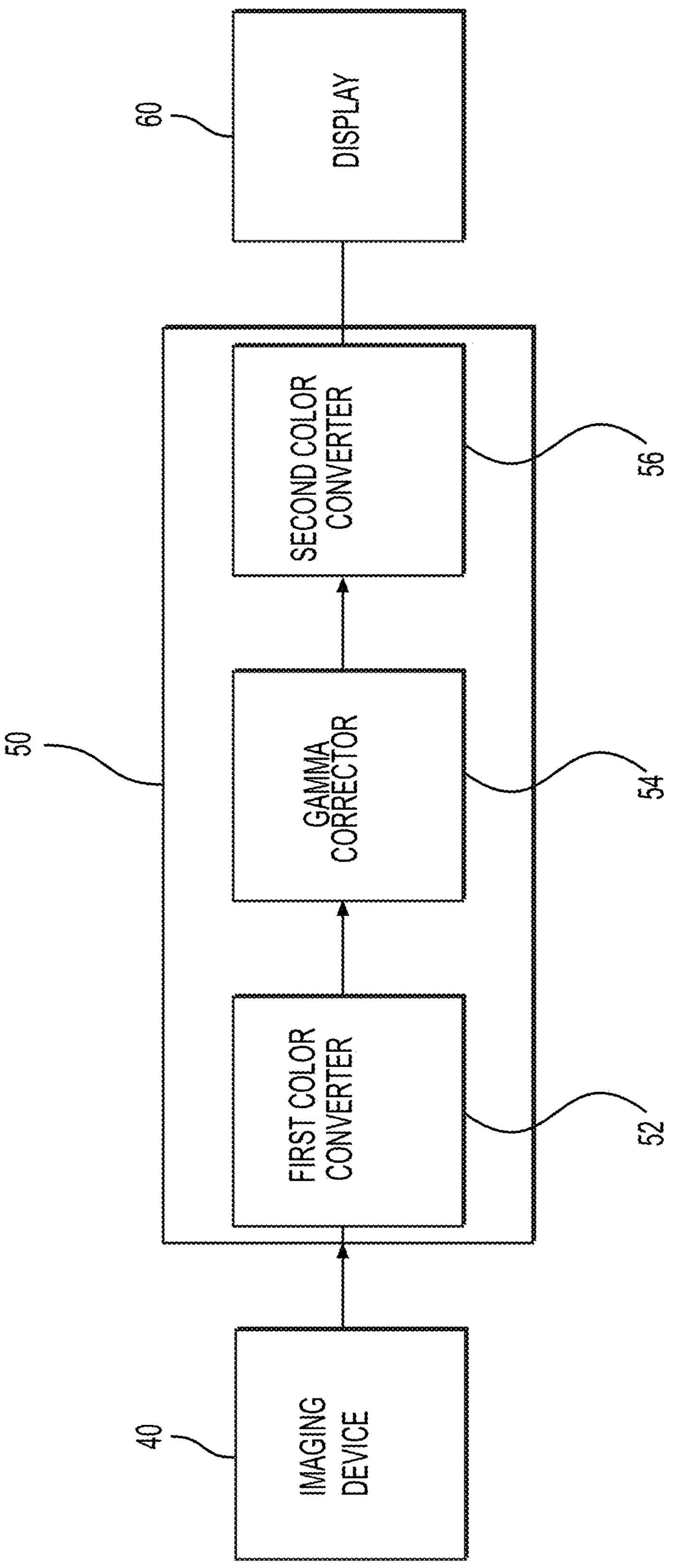
FIG. 2 is a block diagram of a controller of the medical system of FIG. 1 having an input and output.

Controller 50 may control imaging device 40, light emitting device 44, and/or displaying of images on display 60. Controller 50 may be located on or in handle 20, or may be located adjacent handle 20, and may include one or more processors and/or a memory (e.g., memory 80 in FIG. 5). Controller 50 may be configured to implement software and/or instructions (e.g., instructions 110 in FIG. 5) to perform a method of modifying one or more images, as described herein. Controller 50 may also receive instructions from user input device 70. As shown in FIG. 2, controller 50 may include a first color converter 52, a gamma corrector 54, and a second color converter 56. Controller 50 may receive an input from imaging device 40. For example, controller 60 may receive one or more images from imaging device 40 in a RGB format. As will be explained herein, first color converter 52 may convert images in the RGB format to images in a different multi-channel color space or color format, for example in an $YC_bC_r$ format. Gamma corrector 54 then performs an image adjustment process on the images in the $YC_bC_r$ format, as will be explained herein. Subsequently, the processed images are converted back to the RGB format by second color converter 56. Controller 50 may output the processed images in the RGB format to display 60. The one or more processors of controller 50 may carry out the processes of first color converter 52, gamma corrector 54, and second color converter 56.

Controller 50, via gamma corrector 54, modifies or adjusts an image by changing both the chroma (e.g., color) and the luminance or brightness values of pixels in the image using a non-linear gain. That is, a lightness or a brightness value of the pixel may be adjusted separately from chroma, hue, or saturation values of the same pixel. For example, controller 50 calculates a magnitude for a pixel. A magnitude value M is calculated based on a formula, for example the following formula: $M=\sqrt{(Y^2+C_b^2+C_r^2)}$. In this manner, magnitude value M accounts for negative values for Y, $C_b$, and $C_r$ of the pixel in the conversion from the input in RGB format. While a square root formula is described, it will be understood that a magnitude value may be calculated or determined by controller 50 using another formula.

Controller 50 also determines a luminance (luma or brightness) gain and a chroma (e.g., color) gain for each pixel using respective magnitude M. Controller 50 includes an associated memory device (e.g., memory device 80 in FIG. 5) having stored thereon a plurality of look up tables (LUTs) (e.g., LUT 120 in FIG. 5). It will be understood that the LUT may be an equation, a map, or the like. According to an example, a first LUT includes a plurality of luma gain values associated with a plurality of magnitudes M. A second LUT includes a plurality of chroma gain values associated with the plurality of magnitudes M. Once the luma and the chroma gains are determined, controller 50 applies the gain to the luma value. For example, the original luma value may be multiplied by the gain corresponding to the magnitude value M from the luma LUT. Controller 50 also applies the gain to each corresponding chroma value. For example, the original chroma values may be multiplied by the gain corresponding to the magnitude value M from the chroma LUT. In this manner, the luma gain and the chroma gain for each pixel are changed using the same magnitude value M. The magnitude value M may be associated with a same gain value, or a different gain value, in each of the luma and the chroma LUTs.

In some examples, the LUT may provide little to no modification of the original luma or the original chroma values, based on the brightness of the pixel with which those original values are associated (e.g., the gain value may be small or null). In other examples, a maximum luma gain may be approximately 4.5 times the original luma value, and a maximum chroma gain may be approximately 6 times the original chroma value. That is, the brightness of the original values may be appropriate and the luma and chroma values may not be modified. Alternatively, the luma and chroma values may be such that a multiplication factor may be made to one or both of the luma and chroma values to correct an overall brightness of the pixel. It will be understood that the first LUT and the second LUT may be generated during development and may be stored in the memory of controller 50. Alternatively, or additionally, the LUTs may be updated by a software or a hardware update. It will also be understood that the maximum gain values are just examples, and may be altered based on the medical system, the imaging device, and/or other parameters.

According to an example, controller 50 is a field programmable gate array (FGPA). Controller 50 is disposed on medical system 10 (e.g., in or on handle 20) such that image data generated by imaging device 40 is processed by controller 50, and not by a general processing unit (GPU), such as a server remote from medical system 10. The image data is processed by controller 50 to minimize the transmission time between imaging device 40, controller 50, and display 60 to modify the image data within the latency requirements of approximately 150 ms or less. If the image data is transmitted to a GPU, the image data may be unable to be modified within the latency requirements of the medical system 10.

Figure 3:
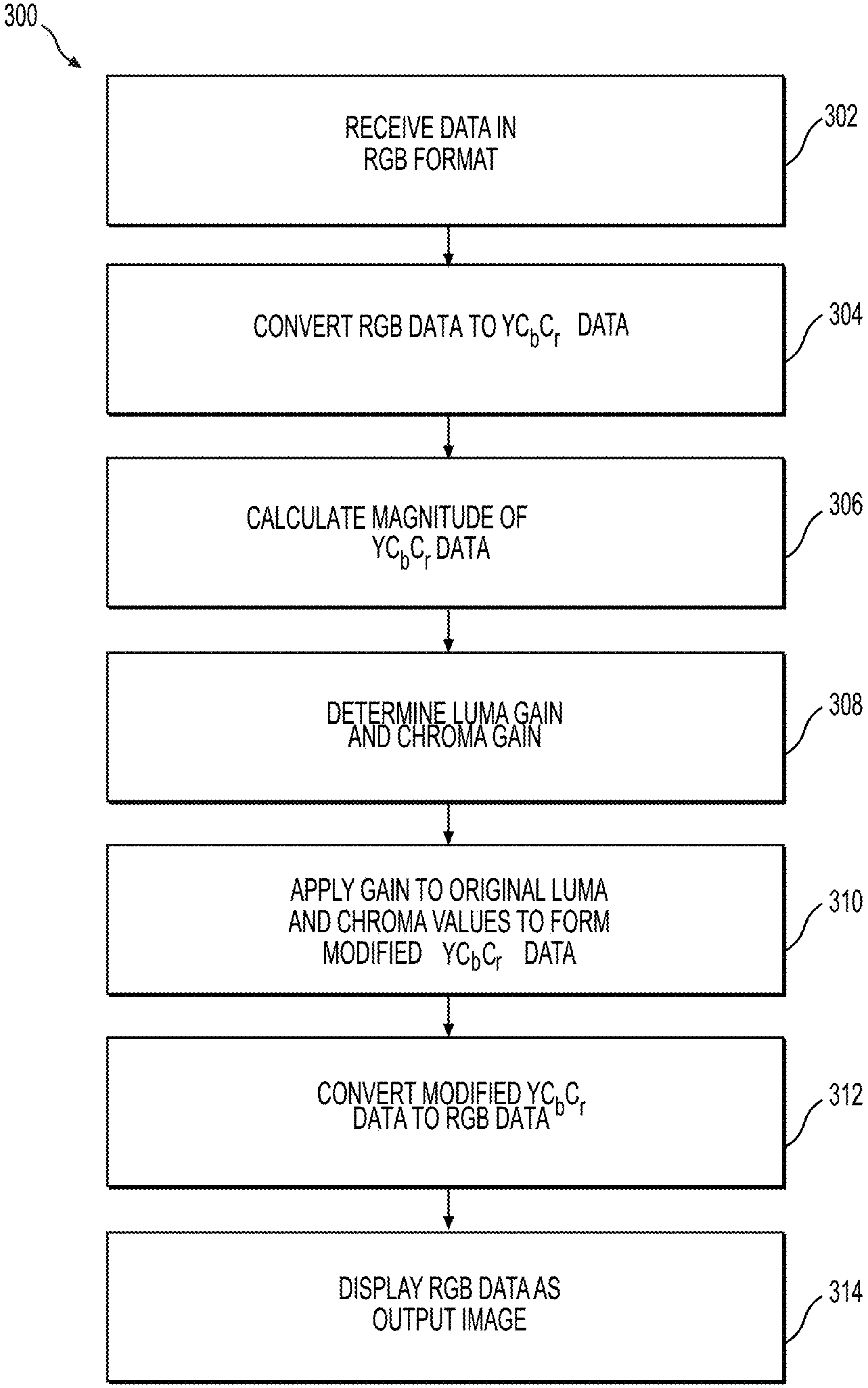
FIG. 3 is a flow chart of a method of enhancing an image of the medical system of FIG. 1.

FIG. 3 is a flow diagram of a method 300 for enhancing a medical image, according to aspects of the disclosure. At step 302, image data generated by imaging device 40 may be received by controller 50. The data generated by imaging device 40 may be provided in the RGB format. Subsequently, controller 50 converts image data, including data for a plurality of individual pixel values, from the RGB pixel format to the $YC_bC_r$ pixel format (e.g., $YC_bC_r$ data) in step 304 by first color converter 52.

In step 306, the pixel magnitude calculation is determined for each pixel. As noted above, the magnitude M is calculated based on the formula $M=\sqrt{(Y^2+C_b^2+C_r^2)}$.

In step 308, the luma gain and the chroma gain are calculated for each pixel using respective magnitude values M calculated in step 308. The memory device of controller 50 includes the plurality of LUTs. The first LUT includes the plurality of luma gain values associated with the plurality of magnitude values M. The second LUT includes the plurality of chroma gain values associated with the plurality of magnitude values M. In this manner, the luma gain and the chroma gain for each pixel are based on the same magnitude values M.

In step 310, the luma gain value is applied to the original Y value of the pixel, and the chroma gain value is applied to each of the original $C_b$ and $C_r$ values of the pixel. That is, each of the original Y values and the original $C_b$ and $C_r$ values are multiplied (e.g., scaled) by respective gain values. As previously described, applying the gain value includes multiplying the original Y value and by the gain value associated with magnitude value M in the luma LUT. Applying the gain value also includes multiplying the original $C_b$ and the original $C_r$ values by the gain value associated with magnitude value M in the chroma LUT. This step provides modified or adjusted Y, $C_b$, and $C_r$ values.

After applying the gain values, the modified or adjusted $YC_bC_r$ pixel values are converted in step 312 from the $YC_bC_r$ format to the RGB format. Subsequently, controller 50 controls an image to be output and displayed on display 60 based on the modified pixel values. It will be understood that steps 306, 308, 310, and 312 may be repeated for each pixel in an image before the image is displayed on display 60. Alternatively, less than all of the image data received from imaging device 40 can be modified by the method 300. While converting a pixel in a RGB format to a $YC_bC_r$ format is described, it will be understood that other multi-channel color formats may be used. For example, the RGB format may be converted to a hue, saturation, value (HSV) format or a hue, saturation, brightness (HSL) format, and the gain may be calculated based on each value of the pixel in the converted format. That is, each channel in a multi-channel color format may be adjusted using a same magnitude based on the values of all channels. In this manner, the luminance or brightness gain and the chroma or color gain for each pixel may be determined based on each channel of the pixel.

Figure 4A:
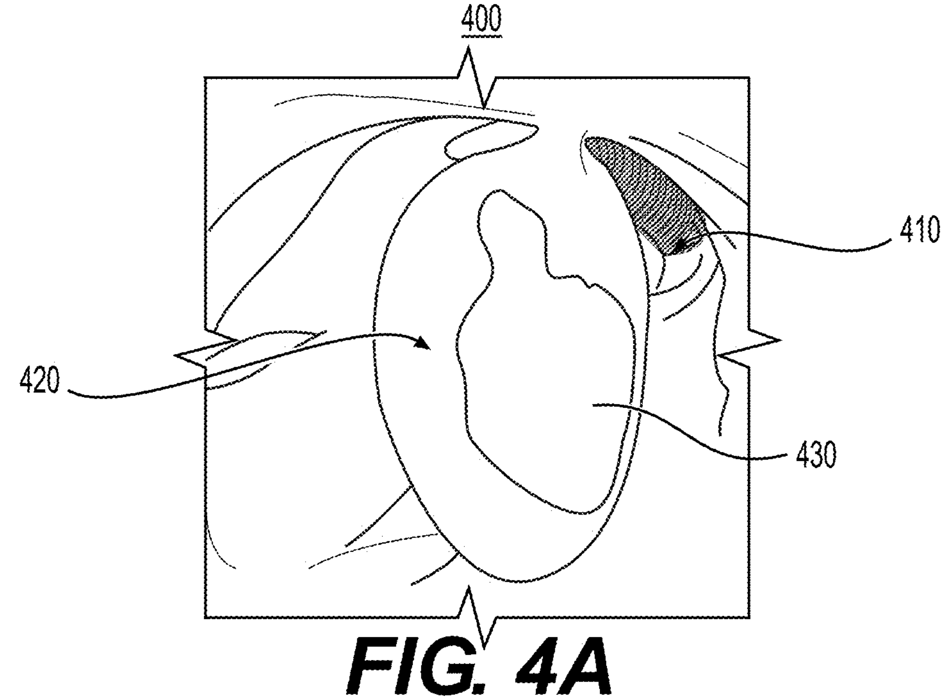
FIG. 4A illustrates an example of an image obtained by the medical system of FIG. 1 without performing a modification.
Figure 4B:
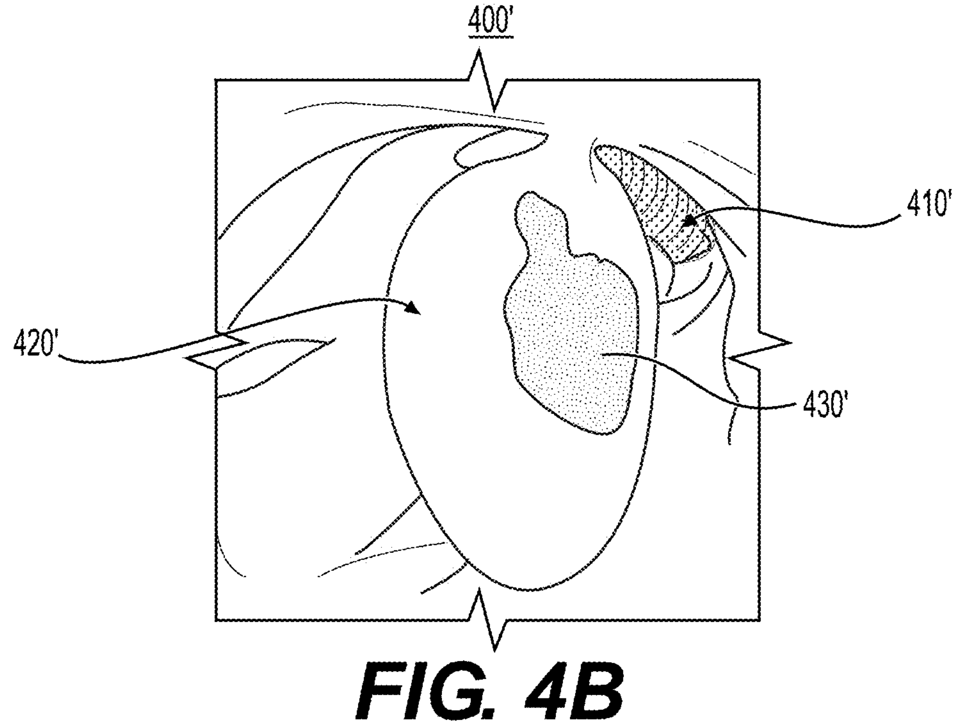
FIG. 4B illustrates an example of an image obtained by the medical system of FIG. 1 after performing a modification.

FIGS. 4A and 4B are example images generated by imaging device 40. FIG. 4A illustrates an image 400 of a target site having a target 420, a "hotspot" 430, and a darker background object 410. Hotspot 430 and background object 410 may be caused by lighting differences at the target site when generating image 400. For example, the position of lighting emitting device 44 (not shown in FIG. 4A) relative to target 420 may cause a greater light intensity on object 420 to generate hotspot 430, and prevent sufficient light to reach background object 410, causing background object 410 to be darker. FIG. 4B illustrates an image 400' that has been modified in the manner described herein. Pixels in an area 430' on a target 420' and a background object 410' have been subjected to a non-linear gain, as described herein. The non-linear gain has decreased the brightness of hotspot 430, to make hotspot 430 more visible as area 430'. Similarly, pixels in background object 410 has been subjected to the non-linear gain to increase the brightness and provide a modified background object 410'. Image 400' may be displayed on display 60, as described herein.

Figure 5:
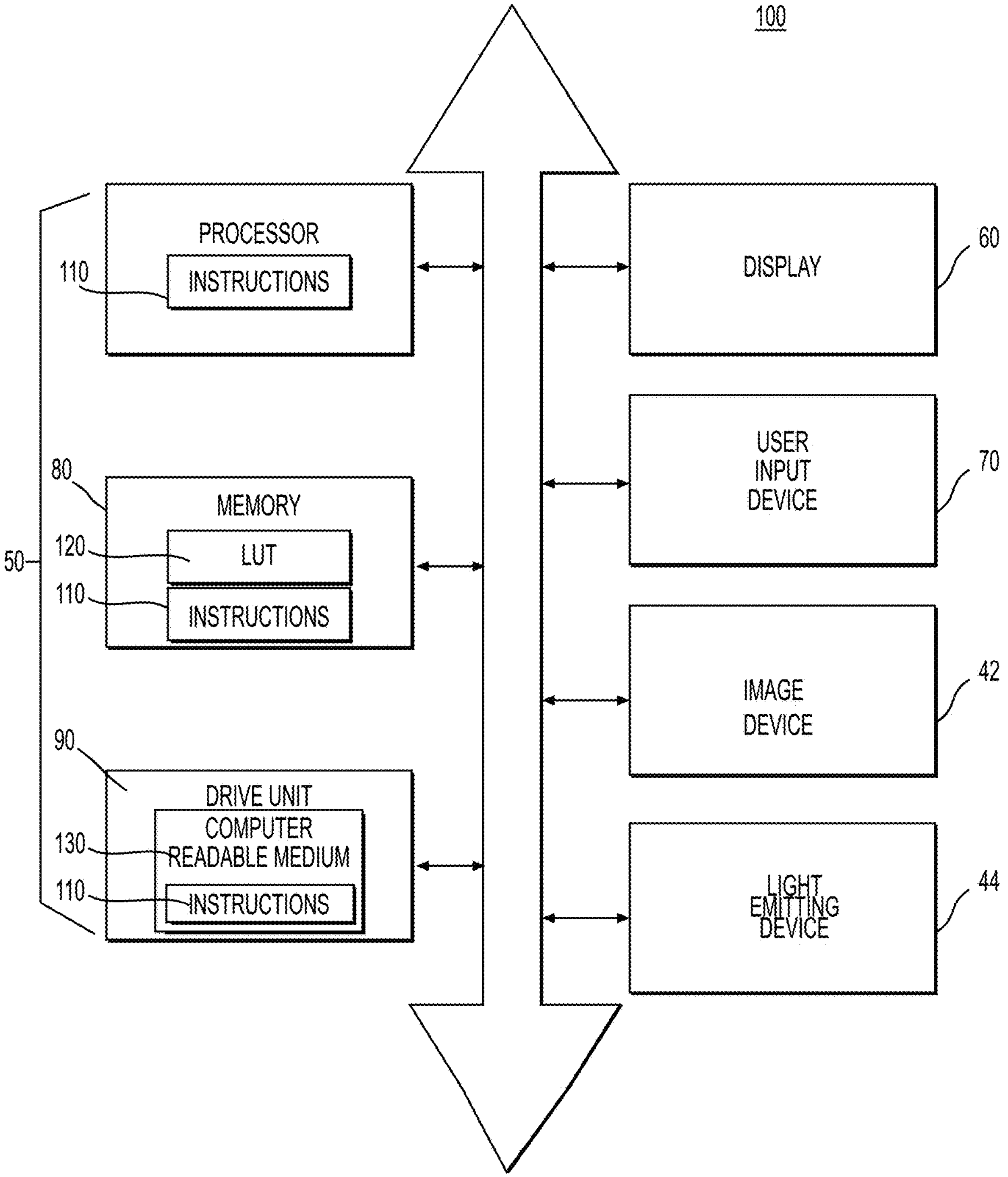
FIG. 5 is an example system that may be used in accordance with techniques described in the medical system of FIG. 1.

FIG. 5 illustrates an exemplary system that may be used in accordance with techniques discussed in FIGS. 1-4, according to aspects of the disclosure. FIG. 5 is a simplified functional block diagram of a computer that may be configured as medical system 10, imaging device 40, and/or user input device 70, according to exemplary embodiments of the disclosure. Specifically, in one embodiment, any of the user devices discussed herein may be an assembly of hardware 100 including, for example, a data communication interface for packet data communication. The platform also may include controller 50, in the form of one or more processors, for executing program instructions 110. The platform may include a storage unit 90 (such as ROM, HDD, SDD, etc.) that may store data on a computer readable medium 130, although the medical system 10 may receive programming and data via network communications. The medical system 10 may also have a memory 80 (such as RAM) storing instructions 110 for executing techniques presented herein, although the instructions 110 may be stored temporarily or permanently within other modules of system 10 (e.g., controller 50 and/or computer readable medium 130). The system 10 also may include input and output ports (e.g., user input device 70, imaging device 42, and/or light emitting device 44) and/or display 60 to connect with input and output devices such as keyboards, mice, touchscreens, monitors, displays, etc. The systems may be implemented by appropriate programming of one computer hardware platform. As discussed herein, it will be understood that the processing of the modified pixels must be performed locally, e.g., on a processor associated with medical system 10, so that it is not necessary to send the image data to a remote processing unit (e.g., a server). In this manner, the latency of the modification of pixels may be improved for the system.

The method and associated imaging systems described herein may improve image generation in a medical system. For example, the magnitude or gain value relies on the overall intensity of each pixel (both the luminance and the chroma values) to determine the appropriate gain value to be applied, thereby providing a non-linear gain. By relying on the non-linear gain, the method may increase visibility of darker areas and hot spots (e.g., for stones in a human body) based on the overall pixel intensity. This preserves the definition of darker colors and preventing a "washed-out" appearance in the image. Further, since this method is a post-processing technique and operates automatically within the medical system, the method may be implemented with any automatic light control feedback loop, using any user selected brightness. Further, the method provides a modified image without competing with lighting or exposure controls, and without the need to change the amount of light at the target site. In addition, the low-complexity of the mathematical equation (e.g., a square root function) enables the method to be performed efficiently using FPGA logic, which can provide for a segmented design, without the need for a GPU. Operating using FPGA logic (e.g., the controller associated with the medical system) enable the image to be modified within the latency parameters of endoscopic imaging devices. Operating within the system latency requirements reduces noticeable jitter on the output image, and allows the method to be implemented with most, if not all, imaging devices associated with endoscopes (e.g., the SpyGlass™ DM System by Boston Scientific Corp.).

It will be apparent to those skilled in the art that various modifications and variations can be made to the disclosed device without departing from the scope of the disclosure. For example, the method of enhancing an image obtained using the camera is not limited to a single camera or medical system. Various imaging and/or light emitting devices, or different medical systems, may be used with the controller to modify an image. It will be understood that the controller and method for enhancing an image described may be used with any scope. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical system, comprising:

a shaft having a proximal end and a distal end;

an imaging device at the distal end of the shaft; and a controller, wherein the controller is configured to:

receive image data comprising pixel data from the imaging device, wherein the pixel data includes one or more values for each of a plurality of individual pixels, wherein the pixel data is in an RGB format, and wherein the pixel data represents one or more hotspots and one or more background portions in an image from the image data, the image comprising other pixel data not representing either of a hotspot or background portion;

convert the pixel data from the RGB format to a YCbCr format;

calculate a magnitude for each of the plurality of individual pixels; and form adjusted pixel data based on applying a non-linear gain to the pixel data, wherein the non-linear gain is based on a Y value, a Cb value, and a Cr value of the plurality of individual pixel values of the converted pixel data, wherein the non-linear gain is a function of the magnitude.

2. The medical system according to claim 1, wherein the magnitude is equal to $\sqrt{(Y^2+Cb^2+Cr^2)}$, and wherein the Y, Cb, and Cr are the Y, Cb, and Cr values of the individual pixels.

3. The medical system according to claim 2, wherein the gain includes a first gain and a second gain, and the first gain is applied to the Y value, and the second gain is applied to both the Cb value and the Cr value of a corresponding individual pixel.

4. The medical system according to claim 2, further comprising a memory, wherein the memory includes a look up table (LUT) for each of a plurality of luminance values and chroma values and wherein the controller is further configured to:

match the magnitude of each individual pixel with a corresponding luminance value based on the plurality of luminance values in the LUT; and form the adjusted pixel data based on chroma values in the LUT for the Cb and Cr values of each individual pixel based on the corresponding luminance value.

5. The medical system according to claim 1, wherein the controller is further configured to convert the adjusted pixel data from the YCbCr format to the RGB format.

6. The medical system according to claim 5, further comprising a display, and wherein the controller is further configured to generate an image based on the adjusted and converted pixel data.

7. The medical system according to claim 1, further comprising a light emitting device at the distal end of the shaft.

8. The medical system according to claim 1, further comprising a user input device configured to receive at least one user input for controlling the medical system.

9. The medical system according to claim 1, wherein the controller includes a field programmable gate array (FPGA).

10. The medical system according to claim 1, wherein the medical system further includes a handle, wherein the controller is disposed on or in the handle.

11. A method of controlling an imaging device for a medical system, the method comprising:

receiving, from the imaging device of the medical system, an image comprising pixel data, wherein the pixel data includes one or more values for each of a plurality of individual pixels, wherein the pixel data is in a first multi-channel color format, and wherein the pixel data represents one or more hotspots and one or more background portions in the image, the image comprising other pixel data not representing either of a hotspot or background portion;

converting the pixel data from the first multi-channel color format to a second multi-channel color format, wherein the second multi-channel color format comprises a brightness value and a color value;

calculating a magnitude for each of the plurality of individual pixels;

applying a non-linear gain to the brightness value and/or color value of the pixel data to form adjusted pixel data; and converting the adjusted pixel data from the second multi-channel color format to the first multi-channel color format to form converted adjusted pixel data, wherein the non-linear gain is a function of the magnitude.

12. The method according to claim 11, wherein the first multi-channel color format is an RGB format and the second multi-channel color format is a YCbCr format, the method further comprising applying a different gain to the brightness value than the color value of corresponding ones of the plurality of individual pixels.

13. The method according to claim 11, further comprising generating an image on a display of the medical system based on the converted adjusted pixel data.

14. The method according to claim 11, wherein applying the non-linear gain to the brightness value and/or color value of the pixel data includes, for each one of the plurality of individual pixels, matching the magnitude with a corresponding brightness value in a brightness look up table (LUT), and matching the brightness value with a corresponding color value in a color LUT.

15. A non-transitory computer-readable medium storing instructions that, when executed by a computer, cause the computer to perform a method for processing electronic images from a medical system, the method including:

receiving an image comprising pixel data from an imaging device of the medical system, wherein the pixel data includes one or more values for each of a plurality of individual pixels, wherein the pixel data is in an RGB format, and wherein the pixel data represents one or more hotspots and one or more background portions in the image, the image comprising other pixel data not representing either of a hotspot or background portion;

converting the pixel data from the RGB format to a YCbCr format;

calculating a magnitude for each of the individual pixels, wherein the magnitude is equal to $\sqrt{(Y^2+Cb^2+Cr^2)}$, and wherein the Y, Cb, and Cr are the Y value, the Cb value, and the Cr value of each respective one of the individual pixels;

applying a gain to adjust a luminance or a chroma for each one of the plurality of individual pixels to form adjusted pixel data, wherein the gain is a function of the magnitude; and converting the adjusted pixel data from the YCbCr format to the RGB format to form converted adjusted pixel data.

16. The non-transitory computer-readable medium of claim 15, the method further comprising applying a different gain to the Y value than the Cb value and the Cr value of a corresponding one of the individual pixels.

17. The non-transitory computer-readable medium of claim 15, the method further comprising generating an image on a display of the medical system based on the converted adjusted pixel data.

* * * * *